Figure 1:
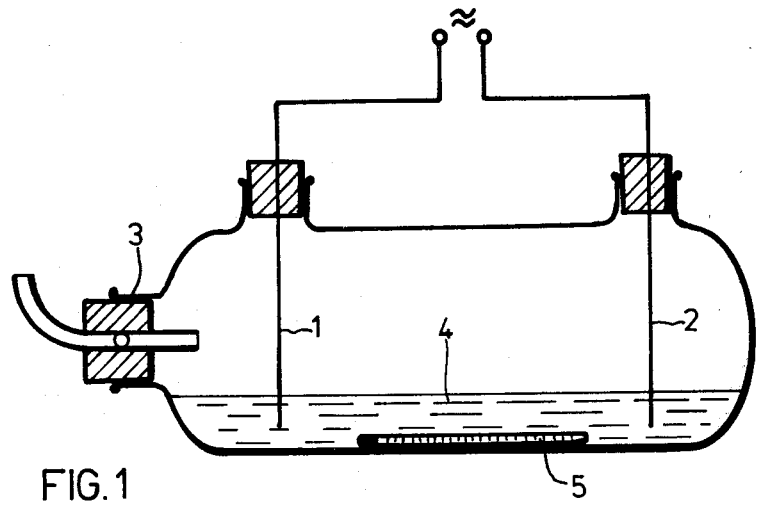

United States Patent [19]

Straub

[11] 4,150,150

[45] Apr. 17, 1979

[54] CARCINOSTATICALLY ACTIVE FORMULATIONS OBTAINED FROM TUMOUR CELLS AND A PROCESS FOR THEIR PREPARATION

[75] Inventor: Otto C. Straub, Tuebingen, Fed. Rep. of Germany

[73] Assignee: Bayer Aktiengesellschaft, Leverkusen, Fed. Rep. of Germany

[21] Appl. No.: 835,922

[22] Filed: Sep. 23, 1977

[30] Foreign Application Priority Data

Sep. 25, 1976 [DE] Fed. Rep. of Germany ....... 2643215

[51] Int. Cl.$^2$ .................. A61K 9/00; A61K 39/00; C12K 9/00
[52] U.S. Cl. .................................... 424/43; 195/1.8; 424/88; 424/95
[58] Field of Search ...................... 195/1.8; 424/95, 88, 424/43

[56] References Cited

U.S. PATENT DOCUMENTS

| 3,526,697 | 9/1970 | Livingston | 424/95 |
| 4,007,086 | 2/1977 | Hamilton | 195/1.8 |
| 4,042,457 | 8/1977 | Kuettner | 195/1.8 |
| 4,053,586 | 10/1977 | Manilla | 424/95 |

Primary Examiner—Sam Rosen
Attorney, Agent, or Firm—Sprung, Felfe, Horn, Lynch & Kramer

[57] ABSTRACT

A method has been developed for the modification of tumour cells by treatment of said tumour cells in aqueous suspension with an alternating electric current so that said tumour cells lose their pathogenic activity and carcinogenic activity and still possess only antigenic activity, stimulating the immunological system against themselves. In addition to the above-described method, the invention also includes the carcinostatically active material obtained by the above-described process, pharmaceutical compositions containing said carcinostatically active material and methods for the treatment of tumours.

15 Claims, 2 Drawing Figures

U.S. Patent    Apr. 17, 1979    4,150,150

CARCINOSTATICALLY ACTIVE FORMULATIONS OBTAINED FROM TUMOUR CELLS AND A PROCESS FOR THEIR PREPARATION

The present invention relates to new carcinostatically active formulations obtained from tumour cells and a process for their preparation.

It has already been disclosed that various tumours can be influenced by means of immunobiological methods. As a rule, these methods are very expensive.

It has now been found that tumour cells can be modified in a simple manner by treatment with an alternating electric current in an aqueous suspension to the effect that they lose their pathogenic activity and carcinogenic activity and only still possess an antigenic action, stimulating the immunological system against themselves.

Furthermore, it has been found that fractions having an immunogenic action can also be isolated by known physicochemical methods from the aqueous tumour cell suspensions treated with an alternating current.

The present invention therefore provides a process for the preparation of carcinostatically active material which comprises the steps of exposing an aqueous suspension of tumour cells to a field of an alternating electric current under sterile conditions, and optionally separating a desired antigen fraction from the treated suspension.

It is new and surprising than an effect of this type can be achieved with tumour cells in such a simple manner with the aid of a field of an alternating electric current.

The invention includes pharmaceutical compositions comprising carcinostatically active material prepared in accordance with the invention and a solid or liquefied gaseous diluent or carrier, or a liquid diluent or carrier containing a surface active agent.

The invention also includes a method of treating tumorous tissue in warm-blooded animals which comprises administering to the said animal carcinostatically active material prepared in accordance with the invention either alone or in admixture with a diluent or carrier.

The process according to the invention is carried out in a reaction vessel under sterile conditions. Two suitable apparatuses which have proved appropriate for this purpose are illustrated (by way of example only) in the accompanying drawings. The apparatus in FIG. 1 comprises a flat glass bottle with three orifices. The orifice at the neck of the bottle (3) is closed by a stopper containing an outlet tube and the other two orifices are also closed by stoppers through which electrodes of a noble metal (for example gold, platinum or silver, preferably silver, noble metal alloys can also be used), which are connected to a source of alternating electric voltage, are passed. A thermometer is located in the bottle for monitoring (5). A suspension of the tumour cells to be treated with the alternating electric current is in the glass vessel. The experimental conditions to be chosen (temperature, period of treatment with the alternating electric current, alternating voltage, current strength, pH value and the like) depend on the nature of the pathogenic and carcinogenic cell material to be treated. Moreover, in some cases there is coupling of the action of the individual factors so that a lower current strength, for example, can be compensated for by a longer period of action of the alternating current.

In order to achieve higher voltage and current strength values, the vessel can also be provided with a cooling jacket.

Figure 2:
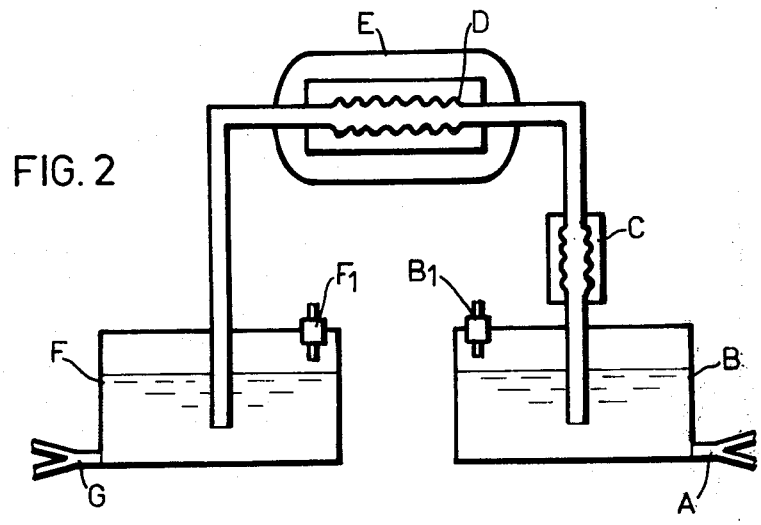

The apparatus shown in FIG. 2 (so-called "flow process") can be characterised in the following manner. In this process, the suspension of tumour cells to be treated flows into the vessel (B) via a two-way cock (A) provided with a valve. The suspension of tumour cells is pumped over the electrodes (D), which are provided with a cooling jacket (E) if appropriate, via the two-way pump (C). The outlet from the vessel (F) is preferably effected via a two-way cock (G) provided with a valve. $B_1$ and $F_1$ denote devices for the air supply and withdrawal respectively. In this procedure, sterile air is appropriately employed.

All the tumours which have been disclosed in the literature can be employed as tumour cells in the process according to the invention; in detail, examples which may be mentioned are: murine leukaemia tumours (for example Ml III and ML IV and EARAD 1), Jensen's sarcoma, Walker sarcoma, carcinoma of the human colon, chondrosarcoma, adenocarcinoma, Rauscher virus leukaemia, various breast tumours, (such as anaplastic tumour, carcinoma solidum, adenocarcinoma, Komedocarcinoma, Paget-carcinoma) Ehrlichcarcinoma, leukaemia L 1210 tumour, breast carcinoma (benzidine-induced), plasmocytoma and others.

In detail, the following process conditions have proved appropriate.

Alternating voltage

In general, the process is appropriately carried out with the existing mains voltage, which was 220 V in our experiments, but it is also possible, of course, to carry out the process with other voltage values, for example 110 or 330 V. In such a case, the other reaction conditions are to be adjusted.

Current strength

A current strength of 200–300 mA with an alternating voltage of 220 V has proved appropriate. Of course, other current strength values are also conceivable as a function of the voltage.

Temperatures

In general, the treatment with the alternating electric current is carried out at temperatures from about 4° to 60° C., preferably at about 20° to 40° C. and in particular at 37° C. (physiological temperature). The temperature used depends, for example, on the heat stability of the tumour cells employed. The temperature of the suspension of tumour cells to be treated can be adjusted, whilst the voltage remains constant, by varying the current strengths in such a manner that there is a constant temperature value in the suspension of tumour cells to be treated.

Period of treatment with the alternating electric current

It has proved appropriate to treat the tumour cells in a field of an alternating electric current for from about 1 to 120 hours, in particular from about 10 to 48 hours. However, time values below 1 or above 120 hours are possible, depending in the nature of the tumour cells employed and the process conditions used (such as, for example, the nature of the electrodes, temperatures, suspending agent, voltage and current strength).

The appropriate solid tumours, which are converted into an aqueous cell suspension with the aid of enzymes, such as, for example, trypsin, by conventional methods may be used as the starting materials. In the case of the leukaemic tumours, the cells which can be isolated from the so-called "buffy coat" are also suitable.

The suspension, obtained according to the process, of the tumour cells treated with an alternating electric current is either administered as such or further separated by conventional physico chemical methods, such as, for example, centrifugation, fractional precipitation, dialysis and the like, in order to isolate definite antigen fractions and is thereafter employed for administration purposes. For this, the tumour cells treated with an alternating electric current, or the antigen fractions optionally isolated from them, were processed to give carcinostatically active formulations, if appropriate with the addition of formulation auxiliaries. When the formulation is intended for parenteral administration, it should be in the form of a sterile and, if appropriate blood isotonic solution.

Formulation auxiliaries of this type which can be used are, for example: excipients, emulsifying agents or dispersing agents such as: water, non-toxic organic solvents or diluents, such as paraffins (for example petroleum fractions), vegetable oils (for example groundnut oil/sesame oil) and polyhydric alcohols, such as glycerol and glycols (for example propylene glycol and polyethylene glycol), solid excipients, such as, for example, natural rock powders (for example highly disperse silica and silicates) and sugars (for example can sugar, lactose and glucose); emulsifying agents, such as non-ionic and anionic emulsifiers (for example polyoxyethylene-fatty acid esters, polyoxyethylene-fatty alcohol ethers, alkylsulphonates and arylsulphonates), dispersing agents (for example lignin, methylcellulose, starch and polyvinylpyrrolidone) and lubricants (for example magnesium stearate, talc, stearic acid and sodium lauryl-sulphate).

The amounts administered in the treatment of the animal organism must be determined from case to case.

The dosage range applicable may vary dependent on the individual tumours and the individual animals to be treated. In case of a suspension of cells containing $10^8$ cells per milliliter, the dosage may range from about 0.05 to about 30 milliliters preferably from about 0.5 to about 15 milliliters per kg body weight of the individual to be treated.

The preferred methods of administration are subcutaneous, intramuscular and intravenous injection, but other methods of administration such as oral administration might be possible too.

EXAMPLE 1 (Preparation of a tumour cell suspension)

NMRI mice with tumours induced by murine leukaemia strain ML III infection are sacrificed by chloroform treatment. With scissors and forceps the solid tumours are exstirpated under sterile conditions and placed into petri dishes. The connecting tissue is removed and the tumours are minced. The minced material is washed twice in a phosphate buffer solution and than transferred into a flask containing a prewarmed 0.25% phosphate-buffered trypsin solution. The suspension is incubated and stirred at 37° C. for 1 hour. The so prepared cell suspension is passed through a gauze filter and than centrifuged at 900 g for 20 minutes. The supernatant is discarded and the sediment is taken up in Hanks' medium containing 0.5% lactalbumin hydrolysate and 3% fetal calf serum. The suspension is stirred for 10 minutes at room temperature (22° C.) and the number of cells per ml in counted (e.g. by a coulter counter). The suspension is centrifuged for 20 minutes at 900 g. The supernatant is discarded and the sediment is taken up in serum-free Hanks-lactalbumin-hydrolysatemedium. This washing procedure is repeated once and the cell amount is adjusted to $5 \times 10^6$ cells per ml.

EXAMPLE 2

An aqueous cell suspension is prepared from tumour cells (murine leukaemia strain ML III, isolated from the solid tumour from NMRI mice) with the aid of trypsin.

This aqueous cell suspension is exposed to a field of an alternating electric current (220 V voltage, 230 mA current strength, silver electrodes) at 57° C. for 24 hours. The following tests were carried out with the tumour cell suspension thus treated.

Immunisation tests using complete murine leukaemia ML III tumour cells modified in the electrical field Procedure A suspension of the cells is prepared which contains $10^7$ cells per 0.1 ml. From this starting suspension, dilutions are prepared in powers of ten, which then contain $10^6, 10^5 \ldots$ etc. to $10^0 = 1$ cell. Mice are then inoculated subcutaneously (0.1 ml per animal) with the starting suspension and the dilution stages and, 6 weeks later, are infected with a dose of $10^7$ untreated tumour cells, (0.1 ml per animal), which as a rule is lethal. The results can be seen in detail in the table which follows. In the first 4 weeks after the infection, the control mice developed tumours and died from them.

Table 1

Results of immunisation tests in mice (strain NMRI) with the aid of tumour cells treated in an electrical field, employing silver electrodes, using leukaemia ML III as an example.

Table 1

| Age of the mice | Number of inoculated mice | Dose (number of cells) | Survival rate dead/living after 6 weeks | Survival rate after exposure to $10^7$ tumour cells dead/living |
|---|---|---|---|---|
| 4 weeks | 10 | $10^7$ | 1/9 | 3/6 |
|  | 10 | $10^6$ | 0/10 | 6/4 |
|  | 10 | $10^5$ | 0/10 | 5/5 |
|  | 10 | $10^4$ | 2/8 | 2/6 |
|  | 10 | $10^3$ | 1/9 | 7/2 |
|  | 10 | $10^2$ | 0/10 | 10/0 |
|  | 10 | $10^1$ | 0/10 | 9/1 |
|  | 10 | $10^0$ | 0/10 | 10/0 |
| 5 days | 10 | $10^7$ | 2/8 | 1/7 |
|  | 10 | $10^6$ | 1/9 | 2/7 |
|  | 10 | $10^5$ | 2/8 | 4/4 |
|  | 10 | $10^4$ | 0/10 | 8/2 |
|  | 10 | $10^3$ | 0/10 | 9/1 |
|  | 10 | $10^2$ | 1/9 | 8/1 |
|  | 10 | $10^1$ | 1/9 | 9/0 |
|  | 10 | $10^0$ | 0/10 | 8/2 |
| 0 days | 10 | $10^4$ | 2/8 | 4/4 |
|  | 10 | $10^3$ | 0/10 | 2/8 |
|  | 10 | $10^2$ | 0/10 | 5/5 |
|  | 10 | $10^1$ | 0/10 | 10/0 |
|  | 10 | $10^0$ | 1/9 | 8/1 |

EXAMPLES 3 and 4

In these Examples antigen fractions are isolated from the suspension of tumour cells, treated with the alternating electric current in accordance with Example 1, as follows:

(1) The cell suspension is centrifuged for 20 minutes at 2,200 g.

(2) The sediment and supernatant liquor are separated and worked up separately: the sediment is worked up to isolate the "small" ether-stable antigen having a molecular weight of 24.000 and called "p 24"; and the supernatant liquor is worked up to isolate the "larger" antigen having a molecular weight of about 60,000 and called "gp" (glycoproteid).

(3) Example 2: Isolation of "p24"

The sediment from (2) is taken up in a borate buffer (pH 8.55) in the ratio 1:8 and homogenised in an icebath with the aid of a mechanical comminuting apparatus (for example Ultraturax) and is then frozen three times at −60° C. and thawed. Centrifugation follows (2,200 g; 10 minutes); 1 part of the supernatant liquor is then mixed with 2 parts of ethyl ether and the mixture is shaken for 30 minutes at 4° C. It is then centrifuged again (2,200 g, 10 minutes), the sediment is discarded and the ether is driven off in vacuo. The residue which remains is used as "p24".

(4) Example 3: Isolation of "gp":

Ammonium sulphate is added to the supernatant liquor from (2) (30 g per 100 ml of supernatant liquor) and stirred for 1 hour. Thereafter, the mixture is stored for 72 hours at +4° C. The clear supernatant liquor is then discarded and the remaining portion is centrifuged for 30 minutes at 1,500 g. The supernatant liquor is again discarded and the sediment is taken up in PBS (phosphate-buffered physiological sodium chloride solution) in an amount which corresponds to one tenth of the starting volume. After storing overnight at 4° C., the mixture is again centrifuged (1,500 g, 15 minutes) and the sediment is discarded. The supernatant liquor is concentrated to 1/100 of the original volume by vacuum dialysis and thereafter is centrifuged for 1 hour at 30,000 g. Purification is then carried out with the aid of a column containing CON-A-Sepharose ®, (an agarose from Messrs. Pharmacia Fine Chemicals, Uppsala, Sweden).

Both antigens are used for detecting antibodies of a specific nature in the case of cattle and murine leucosis (hitherto) or leukaemia and for immunisation.

EXAMPLE 5

Treatment of cancerous mice using "p 24" - and "gp" - fractions isolated from complete murine leukaemia ML III tumour cells modified in the electrical field Four groups (G 1; G 2; G 3; G 4) of 50 4 weeks old mice (strain NMRI) are subcutaneously infected (0.1 ml per animal) with an untreated ML III tumour cell suspension containing $10^7$ cells, which as a rule is lethal.

One week after infection the mice of G 1, G 2 and G 3 are subcutaneously treated with various amounts (G 1=0.3 ml; G 2=0.2 ml; G 3=0.1 ml) of a 1:1 mixture of the "p 24"- and "gp" - fraction isolated from complete ML III tumour cells modified in the electrical field like described in examples 2 and 3. The mice of G 4 are the control animals.

6 weeks later a dose-depending carcinostatic effect can be shown in the treated animal population of G 1, G 2 and G 3 in comparison with the untreated control animals of G 4. (compare with table 2)

Table 2

| Group | Number of infected mice | Dosage ($10^7$ ML III infectious tumour cells/ml) | Survival rate dead/living 1 week after infection | Dosage ml "p24/gp"- fraction | Survival rate dead/living 6 weeks after infection | Percentage of carcinostatic effect |
|---|---|---|---|---|---|---|
| G 1 | 50 | 0.1 | 3/47 | 0,3 | 31/47 | 34 |
| G 2 | 50 | 0,1 | 1/49 | 0,2 | 38/49 | 22 |
| G 3 | 50 | 0,1 | 0/50 | 0,1 | 44/50 | 12 |
| (control) G 4 | 50 | 0,1 | 2/48 | N.D. | 47/48 | |

What is claimed is:

1. A process for the preparation of carcinostatically active material which comprises the steps of exposing an aqueous suspension of tumour cells to a field of an alternating electric current under sterile conditions and separating a desired antigen fraction from the treated suspension.

2. A process of claim 1 wherein the exposure is effected at a temperature of from 4° to 60° C.

3. A process of claim 1 wherein the alternatiing electric current has a voltage of from 110 to 330 volts.

4. A process of claim 1 wherein the alternating electric current has a strength of from 200 to 300 mA.

5. A process of claim 1 wherein the aqueous suspension is exposed to the alternating current for a period of from 1 to 24 hours.

6. A process of claim 1 wherein the exposure to the alternating electric current is effected in essentially the apparatus of FIG. 1.

7. A carcinostatically active material prepared by the process of claim 1.

8. A process of claim 1 wherein the exposure to the alternating current is effected in essentially the apparatus of FIG. 2.

9. A carcinogenicaly active material prepared by the process of claim 8.

10. A pharmaceutical composition comprising an effective amount of a carcinostatically active material of claim 7 and a solid or liquefied gaseous diluent or carrier, or a liquid diluent or carrier containing a surface active agent.

11. A pharmaceutical composition comprising an effective amount of a carcinostatically active material of claim 9 and a solid or liquefied gaseous diluent or carrier, or a liquid diluent or carrier containing a surface active agent.

12. A pharmaceutical composition comprising an effective amount of a carcinostatically active material according to claim 7 in a sterile or blood isotonic aqueous solution or suspension.

13. A pharmaceutical composition comprising an effective amount of a carcinostatically active material according to claim 9 and an inert pharmaceutical carrier.

14. A method of treating tumours in a warm-blodded animal which comprises administering to the said animal an effective amount of a material of claim 7 either alone or in admixture with a diluent or carrier.

15. A method of treating tumours in a warm-blooded animal which comprises administering to the said animal an effective amount of a material of claim 9 either alone or in admixture with a diluent or carrier.

* * * * *